United States Patent
Gadsby et al.

(10) Patent No.: US 6,898,465 B2
(45) Date of Patent: May 24, 2005

(54) DIFFERENTIAL GEL BODY FOR A MEDICAL STIMULATION ELECTRODE

(75) Inventors: Peter Gadsby, East Longmeadow, MA (US); Warren Howland, Chicopee, MA (US)

(73) Assignee: The Ludlow Company IP, Chicopee, MA (US)

( * ) Notice: Subject to any disclaimer, the term of this patent is extended or adjusted under 35 U.S.C. 154(b) by 462 days.

(21) Appl. No.: 09/981,167

(22) Filed: Oct. 17, 2001

(65) Prior Publication Data

US 2003/0074042 A1 Apr. 17, 2003

(51) Int. Cl.$^7$ ................................................. A61N 1/04
(52) U.S. Cl. ........................................ 607/142; 607/152
(58) Field of Search .......................... 600/372, 382, 600/386, 391, 392, 395–397; 607/4–5, 10, 115, 142, 148, 149, 152–153

(56) References Cited

U.S. PATENT DOCUMENTS

| | | |
|---|---|---|
| 3,496,929 A | 3/1967 | Domingues |
| 3,665,064 A | 5/1972 | Mosier et al. |
| 3,817,252 A | 6/1974 | Maurer |
| 4,319,579 A | 3/1982 | Cartmell |
| 4,377,170 A | 3/1983 | Carim |
| 390,067 A | 9/1988 | Chisholm |
| 4,832,036 A | 5/1989 | Cartmell |
| 4,895,169 A * | 1/1990 | Heath .................. 607/142 |
| 5,003,978 A | 4/1991 | Dunseath, Jr. |
| 5,217,014 A | 6/1993 | Hahn et al. |
| 5,295,482 A | 3/1994 | Clare et al. |
| 5,374,283 A | 12/1994 | Flick |
| 5,466,256 A | 11/1995 | McAdams et al. |
| 5,824,033 A * | 10/1998 | Ferrari .................. 607/142 |
| 5,916,244 A | 6/1999 | Walters |
| 6,023,629 A | 2/2000 | Tamada |
| 6,356,779 B1 * | 3/2002 | Katzenmaier et al. ...... 600/391 |
| 6,600,957 B2 * | 7/2003 | Gadsby .................. 607/142 |

* cited by examiner

Primary Examiner—Kennedy Schaetzle
Assistant Examiner—Kristen Mullen
(74) Attorney, Agent, or Firm—RatnerPrestia

(57) ABSTRACT

A pair of disposable medical electrodes for delivering high-energy defibrillation or pacing stimulation are provided and include a positive electrode and a negative electrode. The positive electrode and the negative electrode each include an electrode member with a top face and a bottom face, a electrically conductive coating of a metal and a metal chloride, the coating being disposed on the bottom face, and an electrically conductive gel pad disposed on the coating. The amount of metal chloride included in the coating on the negative electrode is greater than the amount of metal chloride included in the coating on the positive electrode.

30 Claims, 3 Drawing Sheets

DIFFERENTIAL GEL BODY FOR A MEDICAL STIMULATION ELECTRODE

TECHNICAL FIELD

The present invention relates generally to medical electrodes and, more particularly, to disposable medical electrodes intended for high-energy a stimulation (i.e., defibrillation, pacing, and the like) with energy dispersion characteristics.

BACKGROUND OF THE INVENTION

Medical electrodes provide an electrical interface between a patient and monitoring equipment (e.g., an electrocardiograph device) or between a patient and stimulating equipment (e.g., interferential and iontophoresis devices). A specific type of stimulating electrode, used to provide an electrical interface between a patient and defibrillation equipment, must be capable of conducting the high-energy level required for defibrillation. The present invention focuses on high-energy defibrillation and pacing electrodes. The general characteristics of, and distinctions among, monitoring electrodes, general stimulating electrodes, and defibrillation electrodes are outlined below.

A. Monitoring Electrodes

Medical monitoring electrode systems help to obtain desired physiologic responses for the assessment or treatment of diseases and injuries in humans. Monitoring electrodes are used to sense electrical signals, which are then transmitted to electrocardiograph (EKG), electroencephalograph (EEG), and electromyograph (EMG) devices. In general, monitoring electrodes for EKG, EEG, and EMG devices are small, for example on the order of a few square centimeters, because a relatively small contact area with a skin surface is sufficient for reception of electrical signals. Monitoring electrodes need only carry very low electrical signals: on the order of milliamps. In general, monitoring electrodes are not capable of conducting and distributing the high levels of energy required in transcutaneous stimulation and defibrillation electrodes.

B. Stimulating Electrodes

Stimulating electrodes emit electrical pulses for transcutaneous electrical devices, such as transcutaneous electrical nerve stimulation (TENS), electrical muscle stimulation (EMS), neuromuscular stimulation (NMS), functional electrical stimulation (FES), as well as interferential and iontophoresis therapy. Like monitoring electrodes, medical stimulating electrodes are also used to treat diseases and injuries in humans. Unlike and in contrast to monitoring electrodes, however, stimulation electrodes generally require a larger skin surface contact in order to provide sufficient transcutaneous electrical current to effect a desired physiologic response.

Many devices are designed for lower-energy level stimulation applications alone, such as TENS, EMS, NMS, FES, and interferential and iontophoresis therapy. At least some stimulation electrodes are touted as combination electrodes, which can also function as high-energy level defibrillation electrodes. U.S. Pat. No. 5,824,033 issued to Ferrari ("Ferrari") discloses a disposable, multifunction (stimulating or defibrillating), x-ray transmissive electrode capable of conducting energy sufficient for defibrillation and having improved current density distribution between the electrode and the skin of the patient. See column 2, lines 7–13, of the Ferrari patent. Ferrari notes that monitoring electrodes are incapable of conducting and distributing the high levels of energy required in transcutaneous stimulation and defibrillation electrodes; thus, an important distinction exists between high-energy stimulating or defibrillating electrodes and lower-energy stimulating or monitoring electrodes. See column 1, lines 29–32. electrode disclosed in Ferrari includes an electrically conductive metal-metal chloride (e.g., silver-silver chloride) coating applied to one side of a sheet electrode member. See column 3, lines 31–41. Ferrari teaches that the sheet electrode as coated with the electrically conductive metal-metal chloride is not alone capable of transmitting and distributing the high levels of energy encountered in defibrillation over the entire surface of the electrode member. See column 4, line 66 to column 5, line 4. Thus, a current distributing mat is required and is adhered to the opposite side of the sheet electrode member.

The electrode member is a thin, flexible sheet of electrically conductive polymer film having a thickness of two to four mils (0.05 to 0.10 mm). The metal-metal chloride ink is applied in a layer or layers, by silk screening, and is preferably less than ten microns in thickness. See column 4, lines 17–30. The ink may be up to 1 mil (0.0254 mm) thick. The silk screen technique of applying the ink coating facilitates the application of multiple layers having different shapes and edge configurations to achieve a tiered effect. See column 10, lines 10–23.

The outer perimeter of the metal-metal chloride coating is spaced inward from the perimeter of the electrode member and outward from the perimeter of the mat. The metal-metal chloride coating is preferably formed in two layers, each a few microns in thickness. In addition, the layers are serrated or undulated at their outer perimeter. See column 6, lines 12–45.

The electrical conductors in the Ferrari electrode are multi-strand metal wires in which the unsheathed end portions are strands that are spread out and fanned as shown in FIGS. 1 and 3 of Ferrari. The fanned ends are bonded to the surface of the mat by pressing them against the mat and folding the mat over the ends. Specifically, the wires are metallized carbon fiber tows with a metal (e.g., nickel or copper) coating. See column 6, line 46 to column 7, line 40.

C. Defibrillation Electrodes

In a malady called "fibrillation," the normal contractions of a muscle are replaced by rapid, irregular twitchings of muscular fibers (or fibrils). Fibrillation commonly occurs in the atria or ventricles of the heart muscle; the normal, rhythmical contractions of the heart are replaced by rapid, irregular twitchings of the muscular heart wall. A remedy for fibrillation is called "defibrillation," a procedure which applies an electric shock to arrest the fibrillation of the cardiac muscle (atrial or ventricular) and restore the normal heart rhythm. A system of two electrodes, one positive and one negative, is typically used to apply the electrical potential in a defibrillation procedure.

Defibrillation electrodes must be capable of conducting the high-energy level required for defibrillation, up to 360 Joules or more. Defibrillation electrodes must also distribute the energy over a relatively large area of the epidermis of the patient to achieve adequate current density distribution within the atria or ventricles. These characteristics are sufficiently important that governmental regulatory agencies and medical industry groups have established standards for defibrillation electrodes. In particular, the American National Standards Institute (ANSI) standards for defibrillation electrodes have been published by the Association for the Advancement of Medical Instrumentation (AAMI). The ANSI standards for the size of defibrillation electrodes recommend, for example, that the minimum active area of individual, self-adhesive electrodes used for adult defibrillation and pacing shall be at least 50 cm2 and that the total area of the two electrodes shall be at least 150 cm2.

U.S. Pat. No. 5,352,315 issued to Carrier et al. is directed to a biomedical electrode, suitable for defibrillation, that uses a conductive ink to provide varying impedances and at the same time is inexpensively produced and disposable as well. The conductive ink layer or layers may be of the silver and silver chloride type and may be applied by screen printing. The disclosed embodiments provide for the ink blends and ink amounts (i.e., ink thickness and ink pattern) to be varied so that the thickness and pattern provide a particular impedance value suited for the intended placement of the electrode at a particular body site.

A perspective view of another conventional defibrillation electrode construction is shown in FIGS. 2A and 2B. In general, the electrode comprises a sheet electrode member 202 of electrically conductive, carbon-filled polymer; an electrically conductive metal/metal chloride coating 204 (and preferably a silver/silver chloride coating) on at least a major portion of the lower side of the electrode member 202; and a pad of electrically conductive gel 206 underlying the metal/metal chloride coating 204 on the lower side of the electrode member 202. A removable release carrier sheet 208, for example of silicone-coated polyethylene terephthalate (PET), underlies the gel pad 206 and covers the latter before use. The electrode is configured to be x-ray transparent and capable of conducting electrical energy at levels sufficient for defibrillation. The phrase "x-ray transparent" is defined as the quality of being at least substantially invisible at x-ray irradiation levels used in routine x-rays of a patient's chest.

The electrode member 202 is formed of a thin, flexible sheet of electrically conductive polymer film such as graphite-filled polyvinyl chloride film preferably having a thickness of the order of two to four mils (0.05 to 0.10 mm). An example of carbon-filled polymer which can be used is thin, carbon-filled polyvinylchloride (PVC) available from Burkhardt/Freeman, Holyoke, Mass., under the trademark "Conducton." The electrode member 202 has a tab portion 210 with an aperture 212.

The electrode member 202 has a surface area dimensioned to distribute energy over an area of the patient's epidermis to achieve proper current density distribution within the ventricles of the patient's heart. The ANSI standards for the size of defibrillation electrodes published by AAMI recommend that the minimum active area of individual, self-adhesive electrodes used for adult defibrillation and pacing shall be at least 50 cm2 and that the total area of two electrodes used in defibrillation shall be at least 150 cm2. The electrode member 202 has an area of at least 50 cm2 and preferably about 80 cm2 or more so that a pair of the electrodes used for defibrillation can be of the same size.

The coating 204 of metal/metal chloride is typically a conductive ink layer comprising a galvanic metal such as silver, and a conductive salt such as silver chloride. The coating 204 is applied in a layer or layers to the lower face of the electrode member 202 by silk screening or by flexographic printing. A carbon-filled PVC material with silver/silver chloride coating on the underside suitable for use as an electrode member is available from Prime Label And Screen, Inc., New Berlin, Wis. Alternatively, the metal/metal chloride coating 204 can comprise a single layer, chloride-coated metallic foil coated with a conductive acrylic adhesive. The metallic foil may comprise silver, tin, copper, nickel, gold, aluminum, platinum, chromium, cadmium, palladium, zinc, antimony, or indium covered with an adhesive such as the Arclad 8001 bonding tape or Arclad EC2 adhesive. An aperture 214 is provided in the coating 204 and positioned to align with the aperture 212 in the electrode member 202.

An electrolytic gel pad 206 underlies the metal/metal chloride coating 204 on the lower surface of the electrode member 202. The gel pad 206 is preferably a skin-compatible hydrogel having good ability to retain moisture content and adhesive tack. The gel pad 206 is of a type that adhesively connects the electrode to the patient's skin. The gel may comprise, for example, a hydrogel marketed by Ludlow Technical Products (a division of Tyco International Corporation) under the trademark "Procam," product number GRG73P.

At the head 216 of the gel pad 206 are provided a pair of foam tabs 218, and 220. One of the tabs 220 is covered with an adhesive 222. An energy conductor 224 such as a conductive post, stud, or rivet is conductively adhered to the electrode construction. The conductor 224 aligns with, and passes through, both the aperture 214 in the coating 204 and the aperture 212 in the electrode member 202. Such a conductor 224 permits cost-effective use of the electrode with certain defibrillators currently on the market. The conductor 224 may be made of a conductive metal (such as nickel-plated brass or stainless steel) or a conductive plastic. The conductive plastic may be ABS plastic resin, nylon 12, or Carillon polymer crystal resin manufactured by Shell Oil, loaded with 25–40% nickelized carbon fibers. After being molded into its shape, the conductive plastic may be silver-coated (by, e.g., electrolysis) to further enhance its conductivity.

As shown in FIG. 2B, an oversized cover sheet 226 having an adhesive layer on its lower surface is secured to the top of the electrode member 202 (not visibly shown). The cover sheet 226 is x-ray transparent and made of electrically insulative foam such as 0.08 to 0.16 cm thick polyethylene (PE) foam. Shown in FIG. 2B are the two electrodes that form a defibrillation pair of pad electrodes, with cover sheet 226 forming the right pad and cover sheet 228 forming the left pad. The components underlying each of cover sheet 226 and 228 are illustrated in FIG. 2A and discussed above. Cover sheet 226 has an aperture 230 and cover sheet 228 has an aperture 232. Each aperture 230 and 232 aligns with both the aperture 212 in the coating 204 and the aperture 212 in the electrode member 202 respectively underlying the cover sheets 226 and 228 and receives a respective conductor 224. Because the electrodes are x-ray transparent, they can be positioned on the patient at any of the customary positions used for defibrillation without adversely affecting x-rays of the patient's chest in areas underlying the electrodes.

As diagrammatically shown in FIG. 2B, the energy-delivery and energy-accepting electrodes, represented by their respective cover sheets 226 and 228, are connected through conductors 234 and 236 to a connector 238. The connector 238 engages a corresponding connector 240 having lead conductors 242 and 244 which are connected, in turn, to a defibrillator 246. Conductors 234 and 236 of connector 238 are mechanically and electrically connected to the respective energy-delivery and energy-accepting electrodes, through the conductor 224 of each electrode, using a conductive ring contact 248 and a foam ring 250.

The carbon-filled polymer electrode member 202 is conductive in the plane of the electrode and transverse to the plane of the electrode and the metal/metal chloride coating 204 on the under side of the electrode member 202 is also conductive in the plane of the coating and transverse to the plane of the coating. The carbon-filled polymer electrode member 202 has a surface resistance substantially higher than the surface resistance of the metal/metal chloride coating 204 and it has been found that the carbon-filled polymer electrode member 202 with a silver/silver chloride coating 204 is not alone capable of transmitting and distributing the high levels of energy encountered in defibrillation over the entire surface of the electrode member 202.

In addition, published literature indicates that, when a metal plate electrode having an electrolytic gel coating on its underside is placed on the skin and used to deliver current, the current density is very much higher under the perimeter of the electrode than under the center. A similar problem occurs at the energy-accepting electrode of a set of such defibrillation electrodes.

The conventional defibrillation and stimulating electrodes of FIGS. 2A and 2B utilize an electrically conductive metal-metal chloride (i.e. silver-silver chloride) coating 204 applied to one side of a sheet electrode member 202. This design suffers from several shortcomings, including polarization of the electrodes. Upon complete depletion of either metal chloride (i.e. silver chloride) on the negative electrode or metal (i.e. silver) on the positive electrode, electrolysis of water present in the gel pad 206 will begin. Consequently, an acid will be produced at the positive electrode and an alkali will be produced at the negative electrode in the form of H+ and OH−, respectively. These acid and alkali components are then iontophoretically driven into the skin of a patient by current flow, and the result can cause burning of the skin.

It is desirable to provide a mechanism by which the polarization of the electrodes can be resisted, and further, to provide a mechanism to resist the effects of polarization of the electrodes.

SUMMARY OF THE INVENTION

To overcome the above mentioned deficiencies of conventional electrodes, and in view of its purposes, the present invention provides a pair (positive and negative) of disposable medical electrodes that deliver high-energy defibrillation or pacing stimulation and have energy dispersion characteristics. Further, the invention provides an improved disposable medical stimulation electrode that uses different electrode chemistries between the two defibrillation electrodes depending upon the polarity of the signals to which they will be exposed. By providing differential chemistries at each electrode, the invention resists the effects of polarization and improves the current-handling capacity of the electrodes.

The electrodes each include an electrically conductive, carbon-filled polymer electrode member with a top face and a bottom face. An electrically conductive, skin-compatible hydrogel (gel pad) is disposed on at least a major portion of the bottom face of the electrode member. An electrically conductive metal/metal chloride ink coating underlies at least a major portion of the hydrogel on the bottom face of the electrode member. In order to increase the time period in which the electrode pair can resist polarization, the negative electrode is provided with a higher metal chloride (i.e. silver chloride) content in its metal/metal chloride coating than the positive electrode. Finally, the electrode includes a removable release carrier sheet underlying and covering the hydrogel and the electrically conductive ink coating before use of the electrode.

Another aspect of the invention provides for the inclusion of at least one biological buffer in the hydrogel in order to resist the effects of polarization.

It is to be understood that both the foregoing general description and the following detailed description are exemplary, but are not restrictive, of the invention.

BRIEF DESCRIPTION OF THE DRAWINGS

The invention is best understood from the following detailed description when read in connection with the accompanying drawings. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Figure 1:
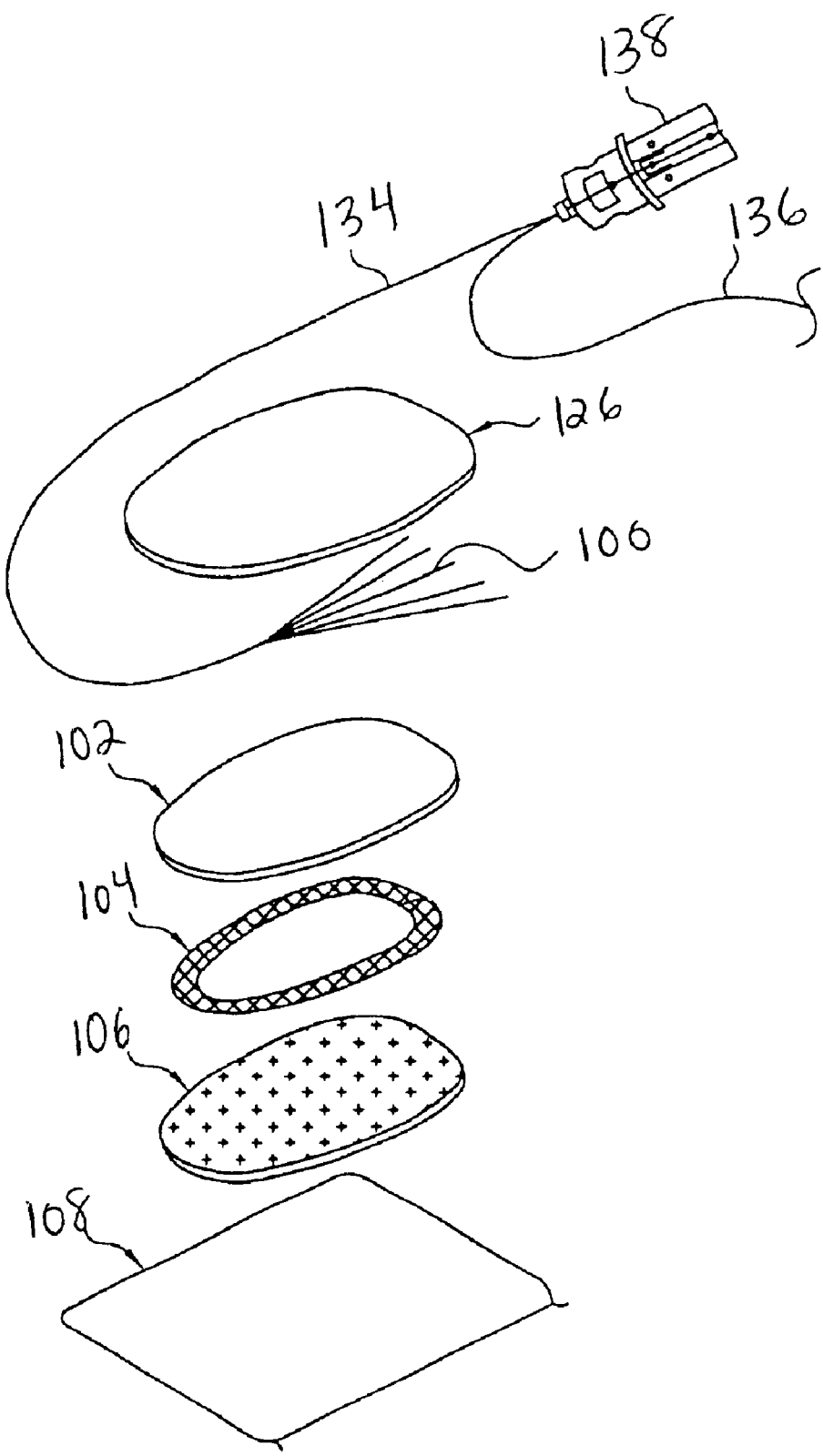
FIG. 1 is a perspective view illustrating the components of the medical defibrillation electrode according to the present invention.
Figure 2A:
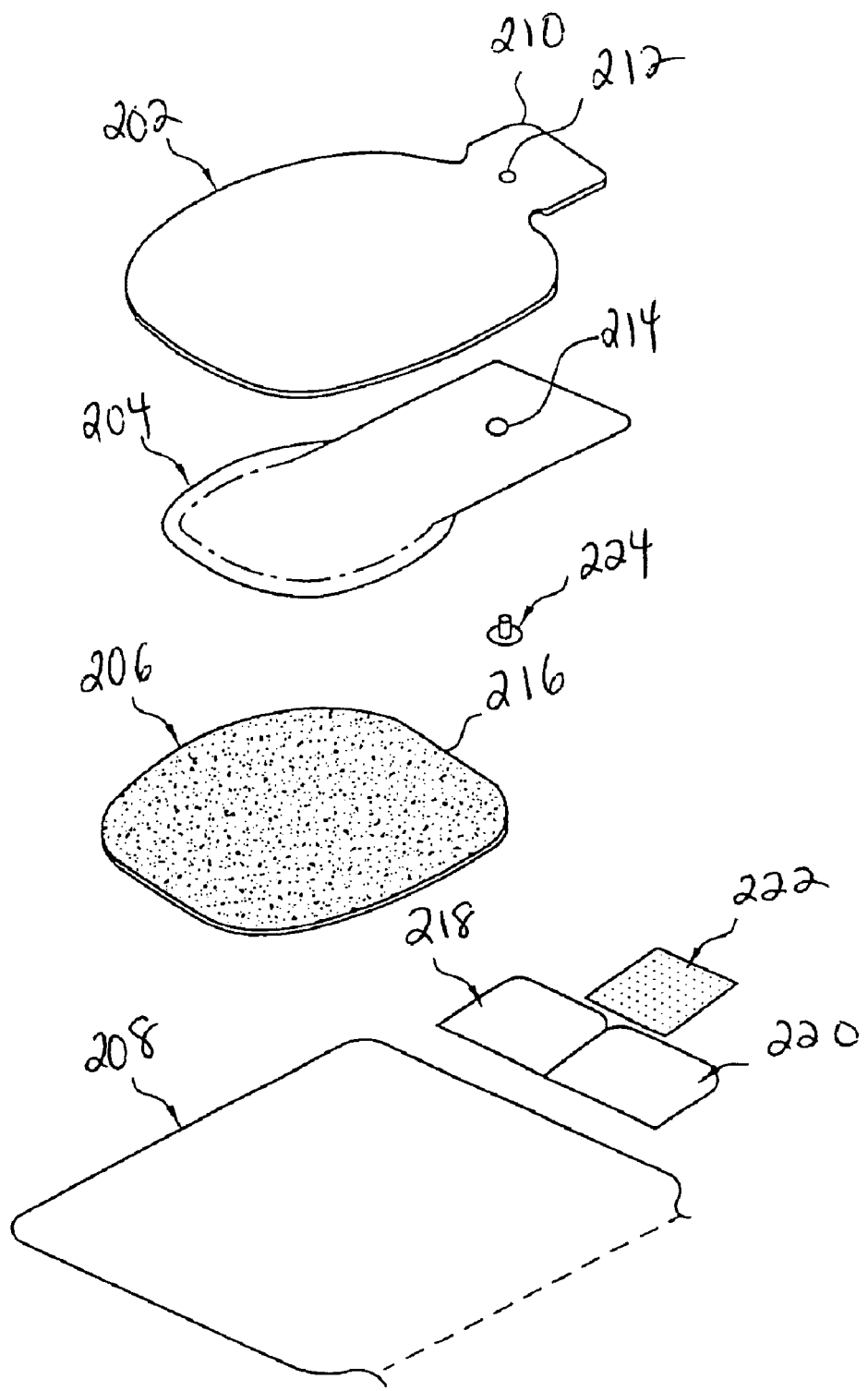
FIG. 2A is a perspective view, with components separated, of a conventional defibrillation electrode construction.
Figure 2B:
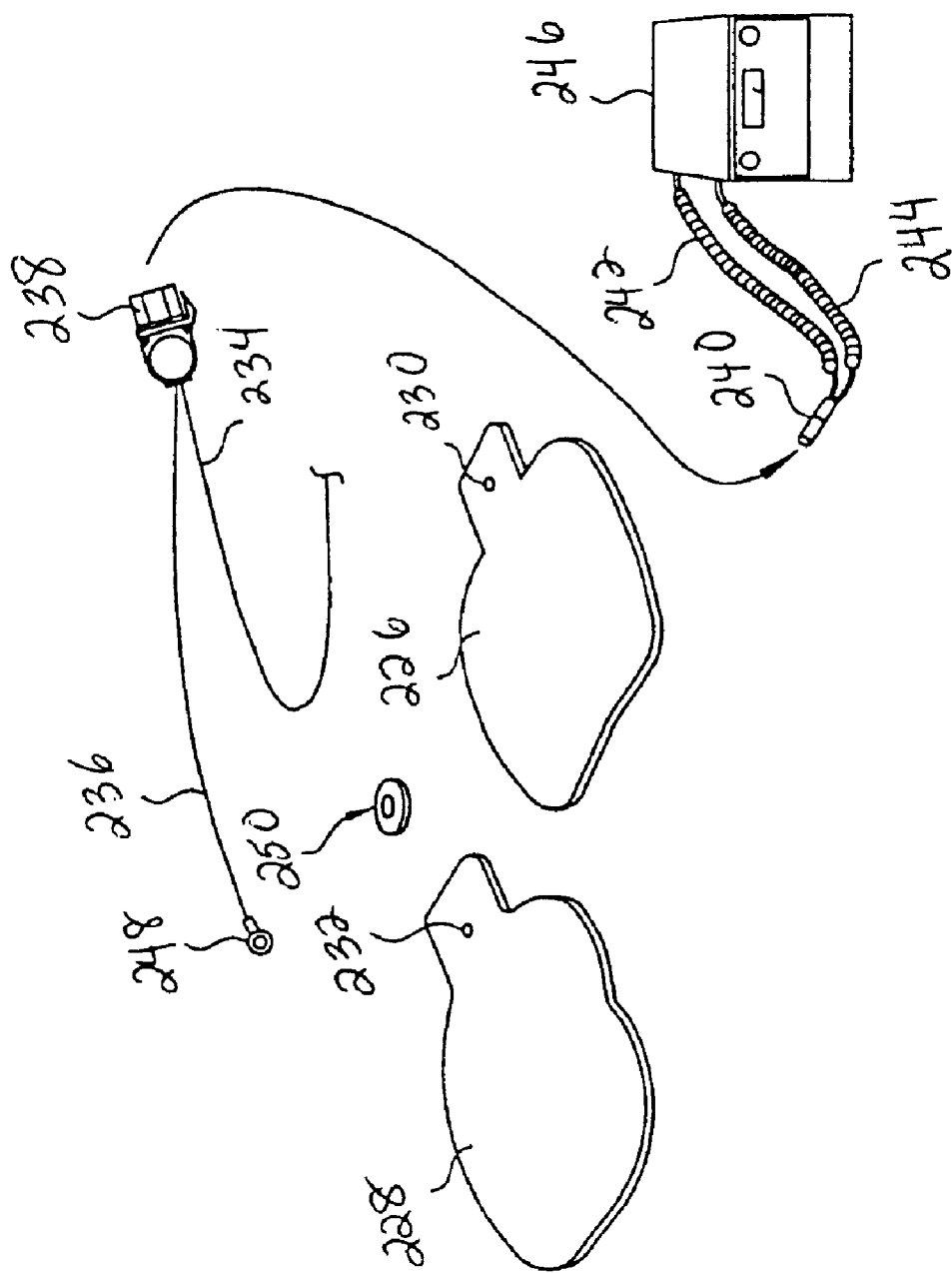
FIG. 2B is a perspective view of (a) conventional cover sheets disposed on top of two conventional electrodes as shown in FIG. 2A, each comprising the underlying components that form a defibrillation pair of pad electrodes, and (b) conventional connections between the electrodes and a defibrillator.

FIG. 1 illustrates a preferred embodiment of the electrode construction according to the present invention. The electrode illustrated in FIG. 1 is representative of either of the positive or negative electrodes of an electrode pair. The electrode construction of FIG. 1 includes a release carrier sheet 108. The release carrier sheet 108 may be made of silicone-coated PET and, although not required, has a rectangular shape. If the shape of the release carrier sheet 108 is rectangular as illustrated, dimensions such as a length of about 165 mm and a width of about 135 mm are suitable.

The electrode construction illustrated in FIG. 1 also includes a cover sheet 126, which is shown with an optional pear-shaped configuration. The cover sheet 126 is a continuous foam backing sheet without any openings and preferably has a thickness of about 1 mm, a major axis of about 156 mm, and a minor axis of about 105 mm. Thus, the cover sheet 126 forms a single peripheral edge for the electrode once the release carrier sheet 108 is removed. An adhesive is provided on the patient-facing side of the cover sheet 126 to releasably affix the release carrier sheet 108 to the cover sheet 126 and, once the release carrier sheet 108 is removed, to releasably affix the electrode to the skin of the patient.

Affixed to the underside of the cover sheet 126 is an electrode member 102. In the exemplary embodiment shown in FIG. 1, electrode member 102 is formed of a thin, flexible sheet of electrically conductive polymer film such as graphite-filled polyvinyl chloride film preferably having a thickness on the order of two to four mils (0.05 to 0.10 mm). Electrode member 102 is shown with an optional pear-shaped configuration with a major axis of about 137 mm, and a minor axis of about 84 mm.

A problem with conventional medical electrodes is polarization of the positive and/or negative electrodes. For example, during use of the electrode pair the metal chloride (i.e. silver chloride) included in the electrically conductive coating in the negative electrode may become depleted. Without the metal chloride in the electrically conductive coating, electrons will begin to stack on the negative electrode, because they can not pass without the metal chloride. In other words, the negative electrode will become polarized.

Conversely, during use of the electrode pair the metal (silver) included in the electrically conductive coating in the positive electrode may be exhausted, resulting in chloride ions stacking on the positive electrode. In other words, the positive electrode will become polarized.

In a conventional electrode pair, both the positive and the negative electrodes have approximately a 10% metal chloride concentration in the electrically conductive coating. As discussed above, the result of the conventional metal chloride concentration is that the negative electrode is going to polarize before the positive electrode polarizes.

As will be discussed in detail below, providing a higher metal chloride (silver chloride) content in the electrically conductive coating in the negative electrode as compared to the positive electrode resists polarization, providing the capacity for the electrode pair to pass current for a longer period of time.

Referring again to FIG. 1, a conductive metal/metal chloride coating 104 (and preferably a silver/silver chloride ink coating) is disposed on the electrode member 102. The length of time that an electrode can resist polarization depends upon the amount of metal chloride present in the coating 104. Upon complete depletion of either metal chloride on the negative electrode or metal on the positive electrode, electrolysis of water present in the gel pad 106 will begin. Consequently, an acid will be produced at the positive electrode and an alkali will be produced at the negative electrode in the form of H+ and OH−, respectively. These acid and alkali components are then iontophoretically driven into the skin of a patient by current flow, and the result can cause burning of the skin.

Therefore, to achieve a first objective of the present invention, there is a higher metal chloride content on the conductive metal/metal chloride coating 104 of the negative electrode as compared to the positive electrode. Therefore, the length of time that an electrode can resist polarization is increased substantially.

The pad of electrically conductive gel 106 is disposed on the coating 104. The gel pad 106 may be approximately the same size and shape as the electrode member 102. The release carrier sheet 108 covers and protects the gel pad 106 and the coating 104 before use.

A conductor 134, which delivers signals to and from the connector 138, engages the electrode. In the embodiment illustrated in FIG. 1, the conductor 134 terminates in a fanned wire 100 that is in direct contact with the back of the carbon-vinyl film electrode member 102. The fanned wire 100 is kept in contact with the electrode member by sandwiching it with the adhesive-coated foam cover sheet 126 which is adhered to the back of the electrode member 102. The termination of conductor 134 in a fanned wire 100 provides a low mass connection relative to alternative conventional connection techniques, as discussed in a U.S. Patent Application entitled HIGH ENERGY DISPOSABLE MEDICAL STIMULATION ELECTRODE with a filing date of Jun. 28, 2001, that is herein incorporated by reference. Further, the fanned wire 100 can be constructed using x-ray transparent material, or alternatively, a conventional metal. Connector 138 also has a separate conductor 136 which engages the second electrode in the defibrillator electrode pair.

Although the first embodiment of the invention discussed above increases the duration that an electrode can resist polarization, polarization of an electrode may ultimately result. Therefore, it is a second objective of the present invention to protect the skin of a patient wearing the electrode pair during polarization. This second novel feature provides resistance to the effects (i.e. burning of skin) of polarization, and includes the use of buffers in the gel pad 106 of the positive electrode to protect against the formation of acid, and buffers in the gel pad 106 of the negative electrode to protect against the formation of hydroxide ions.

During polarization of the electrodes, there is an accompanying breakdown of water, hydroxide ions and hydrogen ions. These ions may be driven into the skin resulting in skin burns. The effect of these ions can be delayed by buffering the gels. The buffering does not resist polarization, but rather resists the effects of polarization, including hydrolysis of the water, which generally leads to burns on the skin.

An exemplary biological buffer useful in the gel pad is piprizene dihydrochloride buffer in combination with glycylglycine buffer. Another exemplary biological buffer useful in the gel pad is a sodium hydrogen maleate buffer. Both of these buffer types work well with the hydrogels of this exemplary embodiment of the present invention and provide an appropriate pH of about 5.2.

The electrically conductive coating 104 may be constructed according to a design disclosed in the U.S. Patent Application entitled HIGH ENERGY DISPOSABLE MEDICAL STIMULATION ELECTRODE. In this alternative embodiment the coating includes a center area with a first conductor thickness. At the outer edge of the center area, the conductor thickness drops to a second conductor thickness. Between the outer edge of the center area and the outer perimeter of the coating 104, the conductor thickness varies according to a predefined gradient. Such a design can be used to provide a desired energy dispersion and current density.

Although illustrated and described above with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A pair of medical electrodes for delivering high-energy defibrillation or stimulation, said pair of electrodes comprising:
   a first electrode including:
      a first electrode member having a first top face and a first bottom face,
      a first electrically conductive coating of a first metal and a first amount of metal chloride, said first coating being disposed on said first bottom face, and
      a first electrically conductive gel pad disposed on said first coating; and
   a second electrode including:
      a second electrode member having a second top face and a second bottom face,
      a second electrically conductive coating of a second metal and a second amount of metal chloride, said second coating being disposed on said second bottom face, said second amount of metal chloride being greater than said first amount of metal chloride, and
      a second electrically conductive gel pad disposed on said second coating;
   said first electrically conductive coating comprises:
      (a) a first center with a first amount of a first conductor, (b) a first inner edge defining the terminus of said first center and a first step at which said conductor drops from said first amount of said first conductor to a second amount of said first conductor, (c) a first outer edge defining the terminus of said first coating and at which said first conductor is substantially absent, and (d) a first predetermined gradient disposed between said first inner edge and said first outer edge; and said second electrically conductive coating comprises:

(a) a second center with a first amount of a second conductor, (b) a second inner edge defining the terminus of said second center and a second step at which said second conductor drops from said first amount of said second conductor to a second amount of said second conductor, (c) a second outer edge defining the terminus of said second coating and at which said second conductor is substantially absent, and (d) a second predetermined gradient disposed between said second inner edge and said second outer edge.

2. The pair of electrodes of claim 1, said first electrode further comprising a first insulative cover sheet disposed on said first top face, and said second electrode further comprising a second insulative cover sheet disposed on said second top face.

3. The pair of electrodes of claim 1 additionally comprising a first electrical connector in contact with said first top face and a second electrical connector in contact with said second top face, said first and second electrical connectors for delivering energy to and transmitting energy from said first and said second electrodes.

4. The pair of electrodes of claim 1, said first electrode further comprising a first removable release carrier sheet disposed on said first gel pad before use of said first electrode, and said second electrode further comprising a second removable release carrier sheet disposed on said second gel pad before use of said second electrode.

5. The pair of electrodes of claim 1, wherein said first metal and said second metal are silver.

6. The pair of electrodes of claim 1, wherein said metal chloride in said first and said second electrically conductive coating is silver chloride.

7. The pair of electrodes of claim 1, wherein said first electrode is a positive electrode and said second electrode is a negative electrode.

8. The pair of electrodes of claim 1, wherein said first electrical connector and said second electrical connector comprise a fanned wire.

9. The pair of electrodes of claim 1 wherein each of said first electrode and said second electrode are an electrically conductive, carbon-filled polymer, and each of said first gel pad and said second gel pad comprises a skin-compatible hydrogel.

10. The pair of electrodes of claim 1 wherein each of said first electrode member and said second electrode member have an area of at least 50 cm2.

11. The pair of electrodes of claim 8, wherein said fanned wire comprises conductive, copper-nickel coated carbon fibers.

12. The pair of electrodes of claim 1 wherein each of said first coating and said second coating is an ink coating.

13. A pair of medical electrodes for delivering high-energy defibrillation or stimulation, said pair of electrodes comprising:

a first electrode including:
a first electrode member having a first top face and a first bottom face,
a first electrically conductive coating of a first metal and a first amount of metal chloride, said first coating being disposed on said first bottom face, and
a first electrically conductive gel pad disposed on said first coating, said first gel pad including a first buffer; and a second electrode including:
a second electrode member having a second top face and a second bottom face,
a second electrically conductive coating of a second metal and a second amount of metal chloride, said second coating being disposed on said second bottom face, and
a second electrically conductive gel pad disposed on said second coating, said second gel pad including, a second buffer;

said first electrically conductive coating comprises:
(a) a first center with a first amount of a first conductor,
(b) a first inner edge defining the terminus of said first center and a first step at which said first conductor drops from said first amount of said first conductor to a second amount of said first conductor,
(c) a first outer edge defining the terminus of said first coating and at which said first conductor is substantially absent, and
(d) a first predetermined gradient disposed between said first inner edge and said first outer edge; and said second electrically conductive coating comprises:
(a) a second center with said first amount of a second conductor,
(b) a second inner edge defining the terminus of said second center and a second step at which said second conductor drops from said first amount of said second conductor to a second amount of said second conductor,
(c) a second outer edge defining the terminus of said second coating and at which said second conductor is substantially absent, and
(d) a second predetermined gradient disposed between said second inner edge and said second outer edge.

14. The pair of electrodes of claim 13 wherein said first buffer is selected from the group consisting of piprizene dihydrochloride in combination with glycylglycine and sodium hydrogen maleate.

15. The pair of electrodes of claim 13 wherein said second buffer is selected from the group consisting of piprizene dihydrochloride in combination with glycylglycine and sodium hydrogen maleate.

16. The pair of electrodes of claim 13 wherein said second amount of metal chloride is greater than said first amount of metal chloride.

17. The pair of electrodes of claim 13, said first electrode further comprising a first insulative cover sheet disposed on said first top face, and said second electrode further comprising a second insulative cover sheet disposed on said second top face.

18. The pair of electrodes of claim 13 additionally comprising a first electrical connector in contact with said first top face and a second electrical connector in contact with said second top face, said first and second electrical connectors for delivering energy to and transmitting energy from said first and said second electrodes respectively.

19. The pair of electrodes of claim 13, said first electrode further comprising a first removable release carrier sheet disposed on said first gel pad before use of said first electrode, and said second electrode further comprising a second removable release carrier sheet disposed on said second gel pad before use of said second electrode.

20. The pair of electrodes of claim 13, wherein said first metal and said second metal are silver.

21. The pair of electrodes of claim 13, wherein said metal chloride in said first and said second electrically conductive coating is silver chloride.

22. The pair of electrodes of claim 13, wherein said first electrode is a positive electrode and said second electrode is a negative electrode.

23. The pair of electrodes of claim 13, wherein said first electrical connector and said second electrical connector comprises a fanned wire.

24. The pair of electrodes of claim 13 wherein each of said first electrode and said second electrode are an electrically conductive, carbon-filled polymer, and each of said first gel pad and said second gel pad comprises a skin-compatible hydrogel.

25. The pair of electrodes of claim 13 wherein each of said first electrode member and said second electrode member have an area of at least 50 cm2.

26. The pair of electrodes of claim 23, wherein said fanned wire comprises conductive, copper-nickel coated carbon fibers.

27. The pair of electrodes of claim 13 wherein each of said first coating and said second coating is an ink coating.

28. The pair of electrodes of claim 1 wherein said first gel pad comprises a first buffer, and said second gel pad comprises a second buffer.

29. The pair of electrodes of claim 28 wherein said first buffer is selected from the group consisting of piprizene dihydrochloride in combination with glycylglycine and sodium hydrogen maleate.

30. The pair of electrodes of claim 28 wherein said second buffer is selected from the group consisting of piprizene dihydrochloride in combination with glycylglycine and sodium hydrogen maleate.

* * * * *